US011160535B2

(12) United States Patent
Yoshimura

(10) Patent No.: US 11,160,535 B2
(45) Date of Patent: Nov. 2, 2021

(54) ULTRASOUND OBSERVATION APPARATUS AND OPERATION METHOD OF ULTRASOUND OBSERVATION APPARATUS

(71) Applicant: OLYMPUS CORPORATION, Tokyo (JP)

(72) Inventor: Takehiro Yoshimura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 224 days.

(21) Appl. No.: 16/514,320

(22) Filed: Jul. 17, 2019

(65) Prior Publication Data

US 2019/0336105 A1 Nov. 7, 2019

Related U.S. Application Data

(63) Continuation of application No. PCT/JP2018/000178, filed on Jan. 9, 2018.

(30) Foreign Application Priority Data

Jan. 23, 2017 (JP) .............................. JP2017-009661

(51) Int. Cl.
*A61B 8/00* (2006.01)
*A61B 8/12* (2006.01)
*A61B 8/14* (2006.01)

(52) U.S. Cl.
CPC ................ *A61B 8/469* (2013.01); *A61B 8/12* (2013.01); *A61B 8/14* (2013.01); *A61B 8/461* (2013.01); *A61B 8/54* (2013.01)

(58) Field of Classification Search
CPC ........... B65D 85/24; F16G 3/08; A61B 8/469; A61B 8/48; A61B 8/12; A61B 8/14;
(Continued)

(56) References Cited

U.S. PATENT DOCUMENTS 8,701,035 B2    4/2014  Hibi et al.
2014/0059486 A1  2/2014  Sasaki et al.
(Continued)

FOREIGN PATENT DOCUMENTS

JP    2010-63548 A    3/2010
JP    2012-121179 A   6/2012
(Continued)

OTHER PUBLICATIONS

International Search Report dated Mar. 20, 2018 issed in PCT/JP2018/000178.

*Primary Examiner* — Joel Lamprecht
(74) *Attorney, Agent, or Firm* — Scully, Scott, Murphy & Presser, P.C.

(57) ABSTRACT

An ultrasound observation apparatus includes: an operation controller configured to control a shape of a region of interest that is set in an ultrasound image according to a change in a contact position at which a contacting object contacts a touch pad, the operation controller being configured to detect two contact positions of the contacting object on the touch pad, calculate a first positional relationship based on the two contact positions in the touch pad, detect a position of the region of interest that is set in the ultrasound image, calculate a second positional relationship based on a position at which the region of interest is set and on a reference position, and control the shape of the region of interest based on a relative relationship between the first positional relationship and the second positional relationship.

11 Claims, 15 Drawing Sheets

(58) Field of Classification Search
CPC ......... A61B 8/461; A61B 8/54; A61B 8/4427; A61B 8/467
See application file for complete search history.

(56) References Cited

U.S. PATENT DOCUMENTS

| | | | |
|---|---|---|---|
| 2015/0141823 A1 | 5/2015 | Lee et al. | |
| 2015/0257738 A1* | 9/2015 | Kim ...................... | A61B 8/483 600/440 |
| 2017/0090571 A1* | 3/2017 | Bjaerum .............. | A61B 8/4254 |
| 2017/0090675 A1* | 3/2017 | Lee ....................... | A61B 8/469 |
| 2018/0021019 A1* | 1/2018 | Jin ....................... | A61B 8/4427 600/437 |
| 2018/0116633 A1* | 5/2018 | Hansen .................... | A61B 8/54 |
| 2018/0203581 A1* | 7/2018 | Takeda .................. | G06F 3/0481 |

FOREIGN PATENT DOCUMENTS

| | | |
|---|---|---|
| JP | 2014-8339 A | 1/2014 |
| JP | 2016-516465 A | 6/2016 |
| WO | WO2014142468 A1 | 9/2014 |

\* cited by examiner

ULTRASOUND OBSERVATION APPARATUS AND OPERATION METHOD OF ULTRASOUND OBSERVATION APPARATUS

CROSS-REFERENCE TO RELATED APPLICATION

This application is a continuation of PCT International Application No. PCT/JP2018/000178, filed on Jan. 9, 2018, which designates the United States, incorporated herein by reference, and which claims the benefit of priority from Japanese Patent Application No. 2017-009661, filed on Jan. 23, 2017, incorporated herein by reference.

BACKGROUND

1. Technical Field

The present disclosure relates to an ultrasound observation apparatus, and an operation method of an ultrasound observation apparatus.

2. Related Art

Ultrasound elastography has been known as a technique to diagnose a subject to be observed using ultrasound. Ultrasound elastography is a technique utilizing difference in hardness between a cancer and tumor tissue in a living body depending on development of a disease and the living body. This technique generates an elasticity image representing, in an image, information on hardness of living tissue by performing coloring using, as a reference value, an average of amounts of displacement of living tissue in a region of interest (ROI) that is set. In ultrasound elastography, an operator sets a region of interest according to the content of observation.

A trackball has been used to operate an ultrasound endoscope; however, in recent years, a touch pad is used from the viewpoint of cleanability. Japanese Laid-open Patent Publication No. 2012-121179 discloses a technique to reduce or increase an area to be selected by a pinch-in operation or a pinch-out operation on a touch pad.

SUMMARY

In some embodiments, provided is an ultrasound observation apparatus configured to cause a display to display an ultrasound image that is generated based on an ultrasound signal that is received from an ultrasound transducer configured to transmit ultrasound to a subject to be observed and receive the ultrasound that is reflected from the subject to be observed. The ultrasound observation apparatus includes: an operation controller configured to control a shape of a region of interest that is set in the ultrasound image according to a change in a contact position at which a contacting object contacts a touch pad, the operation controller being configured to detect two contact positions of the contacting object on the touch pad, calculate a first positional relationship based on the two contact positions in the touch pad, detect a position of the region of interest that is set in the ultrasound image, calculate a second positional relationship based on a position at which the region of interest is set and on a reference position, and control the shape of the region of interest based on a relative relationship between the first positional relationship and the second positional relationship.

In some embodiments, provided is an operation method of an ultrasound observation apparatus configured to cause a display to display an ultrasound image that is generated based on an ultrasound signal that is received from an ultrasound transducer configured to transmit ultrasound to a subject to be observed and receive the ultrasound that is reflected from the subject to be observed. The method includes: by an operation controller, detecting two contact positions at which a contacting object contacts a touch pad; by the operation controller, calculating a first positional relationship based on the two contact positions in the touch pad; by the operation controller, detecting a position of the region of interest that is set in the ultrasound image, by the operation controller, calculating a second positional relationship based on a position at which the region of interest is set and on a reference position; and by the operation controller, controlling a shape of the region of interest that is set in the ultrasound image based on a relative relationship between the first positional relationship and the second positional relationship.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
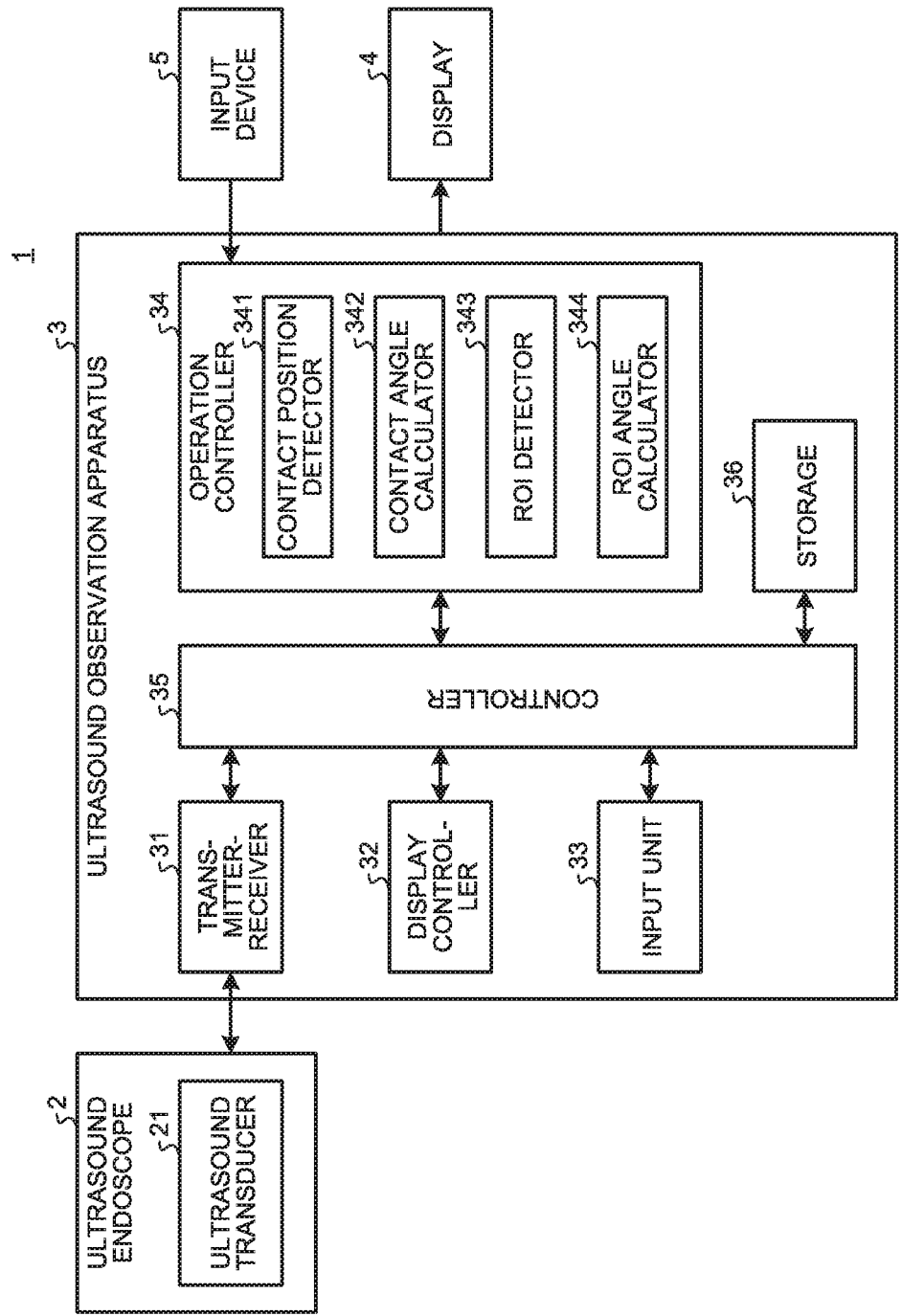
FIG. 1 is a block diagram illustrating a configuration of an ultrasound diagnostic system including an ultrasound observation apparatus according to a first embodiment of the present disclosure.

Embodiments of an ultrasound observation apparatus, an operation method of an ultrasound observation apparatus, and an operation program for an ultrasound observation apparatus according to the present disclosure will be described with reference to the drawings. The embodiments do not limit the disclosure. The following embodiments will be described by exemplifying an ultrasound diagnostic system including an ultrasound endoscope, and the disclosure is applicable generally to ultrasound diagnostic systems, such as external ultrasound diagnostic systems and industrial ultrasound diagnostic systems.

As for illustration in the drawings, like or corresponding components are denoted with like reference numerals as appropriate. Furthermore, it should be noted that the drawings are schematic and thus the relationship in size among components and the ratio among components can differ from actual ones. The drawings may also contain parts whose relationship in size or ratio differ among the drawings.

First Embodiment

FIG. 1 is a block diagram illustrating a configuration of an ultrasound diagnostic system including an ultrasound observation apparatus according to a first embodiment of the disclosure. As illustrated in FIG. 1, an ultrasound diagnostic system 1 includes an ultrasound endoscope 2 that transmits ultrasound to a subject to be observed and receives the ultrasound reflected from the subject; an ultrasound observation apparatus 3 that generates an ultrasound image based on an ultrasound signal that is acquired by the ultrasound endoscope 2; a display 4 that displays the ultrasound image that is generated by the ultrasound observation apparatus 3; and an input device 5 that accepts an input of an instruction signal for setting an observation mode, setting an observation condition, or the like, in the ultrasound observation apparatus 3.

Figure 2:
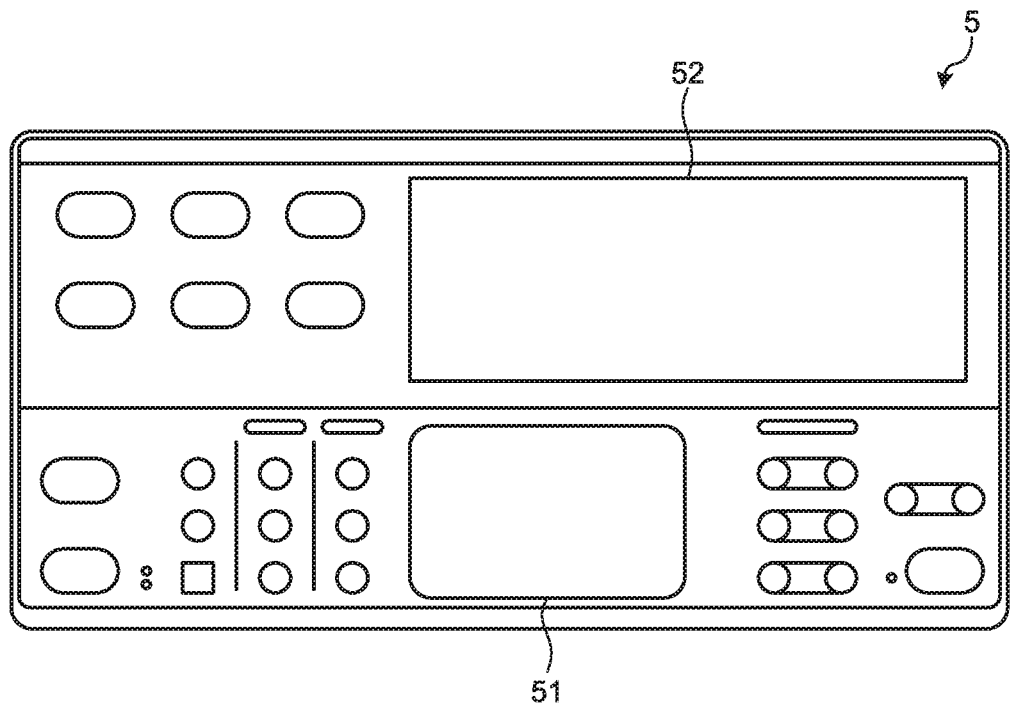
FIG. 2 is a diagram illustrating a configuration of the input device illustrated in FIG. 1.
Figure 3:
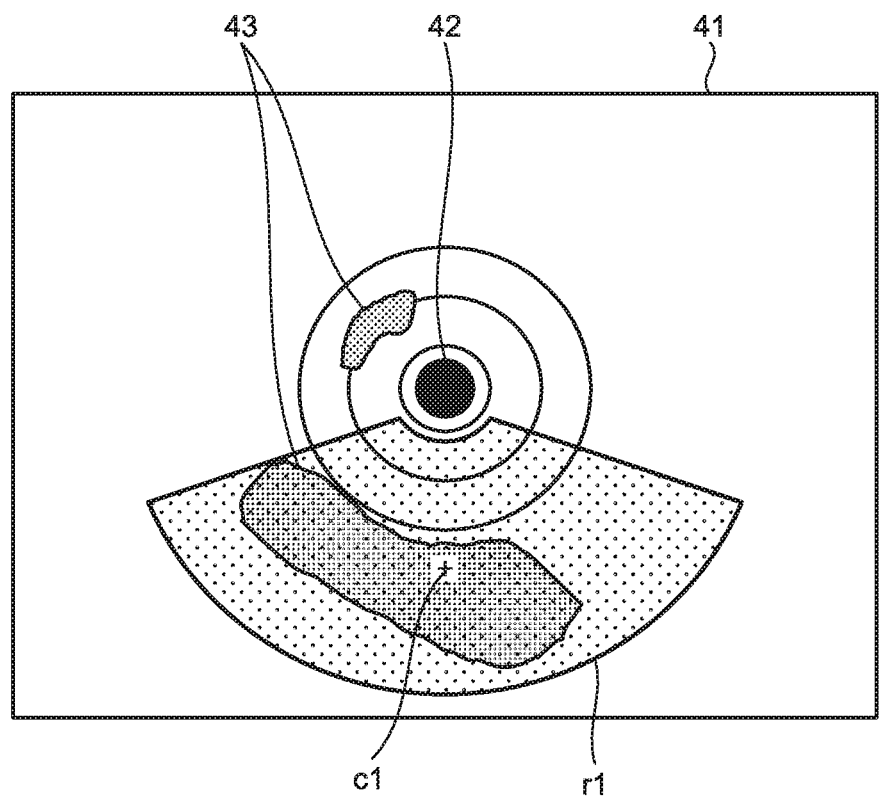
FIG. 3 is a diagram illustrating that an ROI is set in a lower part of an ultrasound image.

FIG. 2 is a diagram illustrating a configuration of the input device illustrated in FIG. 1. FIG. 3 is a diagram illustrating that an ROI is set in a lower part of an ultrasound image. In the ultrasound diagnostic system 1, an operator performs an operation on a touch pad 51 of the input device 5 that is illustrated in FIG. 2, thereby reducing or increasing an ROI r1 that is set in an ultrasound image 41 illustrated in FIG. 3.

The ultrasound endoscope 2 includes an ultrasound transducer 21 at its head and the ultrasound transducer 21 converts an electric signal that is received from the ultrasound observation apparatus 3 into an ultrasound pulse (acoustic pulse) and applies the ultrasound pulse to a subject and converts ultrasound echo that is reflected from the subject into an electric echo signal (ultrasound signal) representing the ultrasound echo by a change in voltage and outputs the echo signal. The ultrasound transducer 21 is achieved with a radial-type ultrasound transducer. In the ultrasound endoscope 2, the ultrasound transducer 21 may be caused to perform mechanical scanning, or a plurality of elements may be provided in an array as the ultrasound transducer 21 and the ultrasound transducer 21 may be caused to perform electric scanning by electrically switching the elements relating to transmission and reception and delaying the transmission and reception at each of the elements.

The ultrasound endoscope 2 normally includes an imaging unit including an imaging optical system and an imaging device, and the ultrasound endoscope 2 is inserted into a digestive tract of the subject (the esophagus, the stomach, the duodenum or the large intestine) or a respiratory organ (the trachea or a bronchi), enabling image capturing on the digestive tract or the respiratory organ and their surroundings organs (the pancreas, the gallbladder, the bile duct, the bile tract, lymph nodes, mediastinal organs, blood vessels, etc.). The ultrasound endoscope 2 includes a light guide that guides illumination light that is applied to the subject to capture an image. While the head of the light guide reaches the head of a part to be inserted into the subject, the proximal end of the light guide is connected to a light source device that generates the illumination light.

The ultrasound observation apparatus 3 includes a transmitter-receiver 31, a display controller 32, an input unit 33, an operation controller 34, a controller 35, and a storage 36.

The transmitter-receiver 31 transmits and receives electric signals from and to the imaging unit and the ultrasound transducer 21. The transmitter-receiver 31 is electrically connected to the imaging unit and transmits imaging information, such as imaging timing, to the imaging unit and receives an imaging signal that is generated by the imaging unit. Furthermore, the transmitter-receiver 31 is electrically connected to the ultrasound transducer 21 and the transmitter-receiver 31 transmits an electric pulse signal to the ultrasound transducer 21 and receives an echo signal that is an electric reception signal from the ultrasound transducer 21. Specifically, the transmitter-receiver 31 generates an electric pulse signal based on a waveform and transmission timing that are set previously and transmits the generated pulse signal to the ultrasound transducer 21.

The transmitter-receiver 31 performs sensitivity time control (STC) correction in which an echo signal with a deeper hydrophone depth is amplified at a higher amplification rate. After performing processing, such as filtering, on the amplified echo signal, the transmitter-receiver 31 performs A/D conversion to generate a time-domain digital radio frequency (RF) signal and outputs the RF signal.

The display controller 32 generates endoscopic image data based on the imaging signal and ultrasound image data corresponding to the electric echo signal. Furthermore, the display controller 32 superimposes various types of information on the endoscopic image data and the ultrasound image data and outputs the data with various types of information superimposed thereon to control display on the display 4. The display controller 32 is achieved using a central processing unit (CPU) having operational and control functions and various types of operational circuits.

The input unit 33 receives instruction signals that are input by the input device 5 and accepts input of various types of information corresponding to the received instruction signals. As the various types of information, observation mode setting and observation condition setting (for example, switching between gain and display range and scroll instruction information (a slide direction and an a slide amount of a B-mode image)), rotation instruction information (a rotation direction and a rotation amount of the ultrasound image 41) are exemplified.

The operation controller 34 controls the shape of the ROI that is set in the ultrasound image 41 according to a change in a contact position at which a contacting object such as a finger of an operator contacts the touch pad 51 of the input device 5. The controller 35 is achieved using a CPU with operational and control functions and various operational circuits.

The operation controller 34 includes a contact position detector 341 that detects a contact position of an object contacting the touch pad 51; a contact angle calculator 342 that calculates a first positional relationship based on two contact positions in the touch pad 51; an ROI detector 343 that detects a position of an ROI that is set in the ultrasound image 41; and an ROI angle calculator 344 that calculates a second positional relationship based on a position at which the ROI is set and a reference position. The operation controller 34 controls the shape of the ROI based on a relative relationship between the first positional relationship, which is calculated by the contact angle calculator 342, and the second positional relationship, which is calculated by the ROI angle calculator 344, and on a time change in contact position that is detected by the contact position detector 341.

Figure 4:
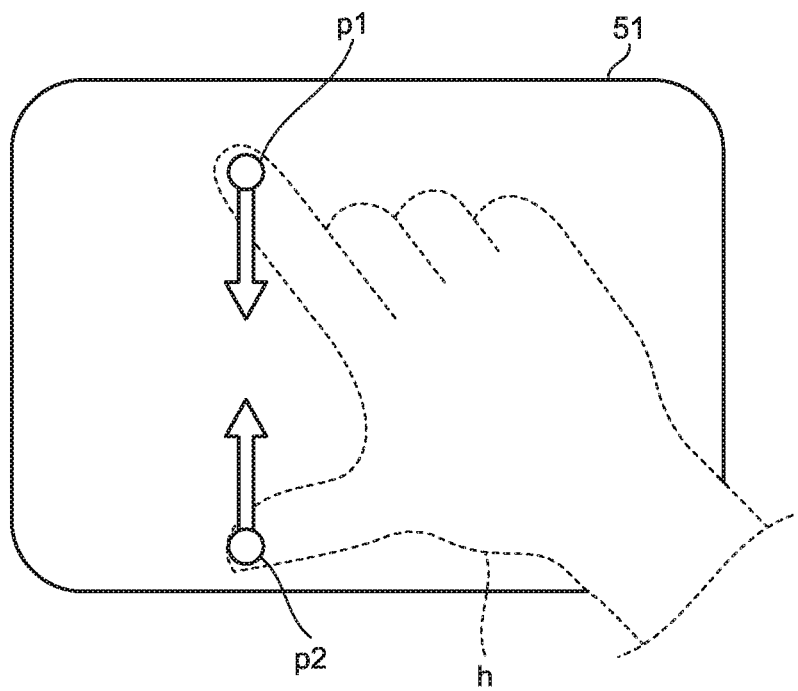
FIG. 4 is a diagram illustrating that an operator performs a pinch-in operation in the vertical direction on an operation screen of a touch pad.

Under the control of the controller 35, the contact position detector 341 detects the contact position of the contacting object that is caused by the operator to make contact with the touch pad 51 of the input device 5. FIG. 4 is a diagram illustrating that an operator performs a pinch-in operation in the vertical direction on an operation screen of the touch pad. As illustrated in FIG. 4, when a hand h of the operator gets close to the touch pad 51 of the input device 5 and fingers of the operator make contact with the operation screen of the touch pad 51 at two points, the contact position detector 341 detects a point p1 and a point p2 that are contact positions of the fingers. Furthermore, when the operator moves the contact positions of the fingers, the contact position detector 341 repeatedly detects the moved contact positions at regular intervals.

Under the control of the controller 35, the contact angle calculator 342 calculates the first positional relationship. The first positional relationship is an angle (a contact angle below) formed by a first straight line and a reference line, the first straight line passing through the centers of the two contact positions (the point p1 and the point p2) in the touch pad 51. The reference line is, for example, a straight line corresponding to a horizontal side of the rectangular operation screen of the touch pad 51. Alternatively, the reference line may be a straight line corresponding to a vertical side of the operation screen, and how to set a reference line is not particularly limited.

Figure 5:
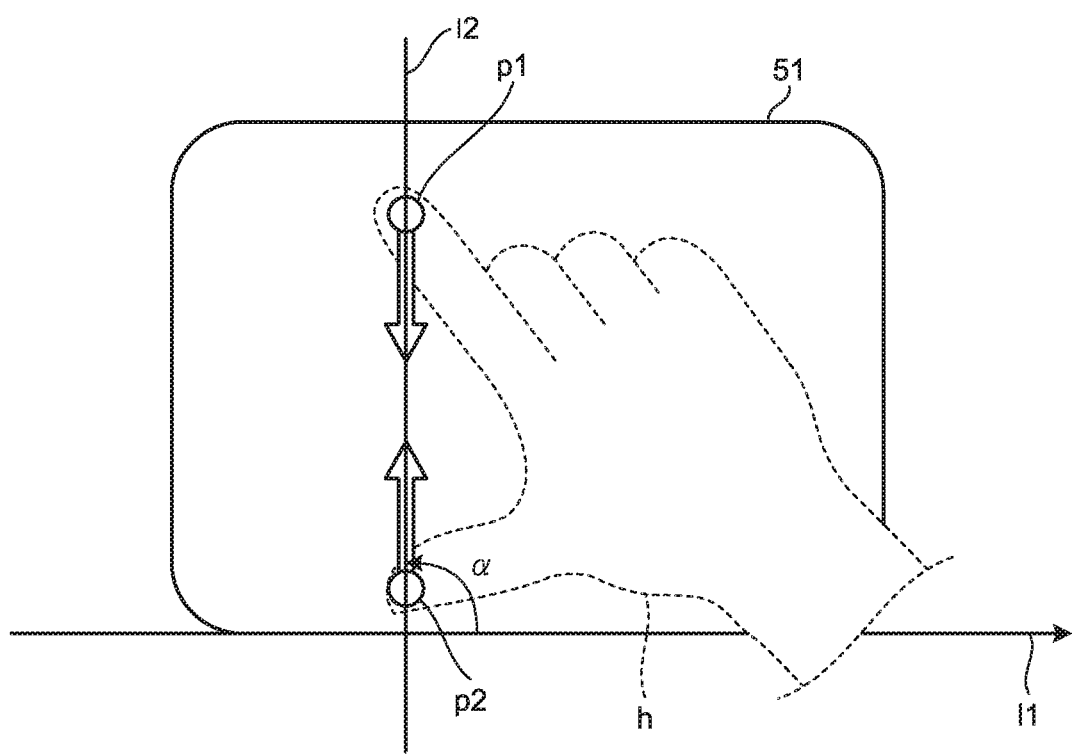
FIG. 5 is a diagram for explaining a contact angle.

FIG. 5 is a diagram for explaining a contact angle. As illustrated in FIG. 5, an angle formed by a straight line l1 (reference line) corresponding to the horizontal side of the rectangular operation screen of the touch pad 51 and a straight line l2 (the first straight line) passing through the center of the point p1 and the center of the point p2 is a contact angle α. For the angle formed by the straight line l1 and the straight line l2, the contact angle α with respect to the straight line l1 is defined within a range of 0°≤α≤180°, with the counterclockwise direction being set as a positive direction.

Under the control of the controller 35, the ROI detector 343 detects the position of the ROI that is set in the ultrasound image 41. The position of the ROI is, for example, the center of the ROI. As illustrated in FIG. 3, the ultrasound image 41 contains an ultrasound transducer area 42 corresponding to the ultrasound transducer 21 and an examination subject area 43 to be examined, such as a tumor, and the ROI r1 is superimposed on the ultrasound image 41. The ROI r1 forms a shape obtained by excluding a circular sector with a smaller radius of two circular sectors about the central position of the ultrasound transducer area 42, which are circular sectors having a same central angle but having different radii, from a circular sector with a larger radius of the two circular sectors. A center c1 of the ROI r1 is a point at the center of the ROI r1 in the radial direction of the ultrasound transducer area 42 and in the azimuth direction of the ultrasound transducer area 42. The shape of the ROI is not particularly limited and the shape may be trapezoid or a polygon that is arranged radially from the central position of the ultrasound transducer area 42.

Under the control of the controller 35, the ROI angle calculator 344 calculates the second positional relationship. The second positional relationship is an angle (ROI angle below) formed by a second straight line and the reference line, the second straight line passing through the center c1 of the ROI r1 and the reference position. The reference position is, for example, the central positon of the ultrasound transducer area 42. The reference line is a straight line corresponding to the straight line l1 in FIG. 5.

Figure 6:
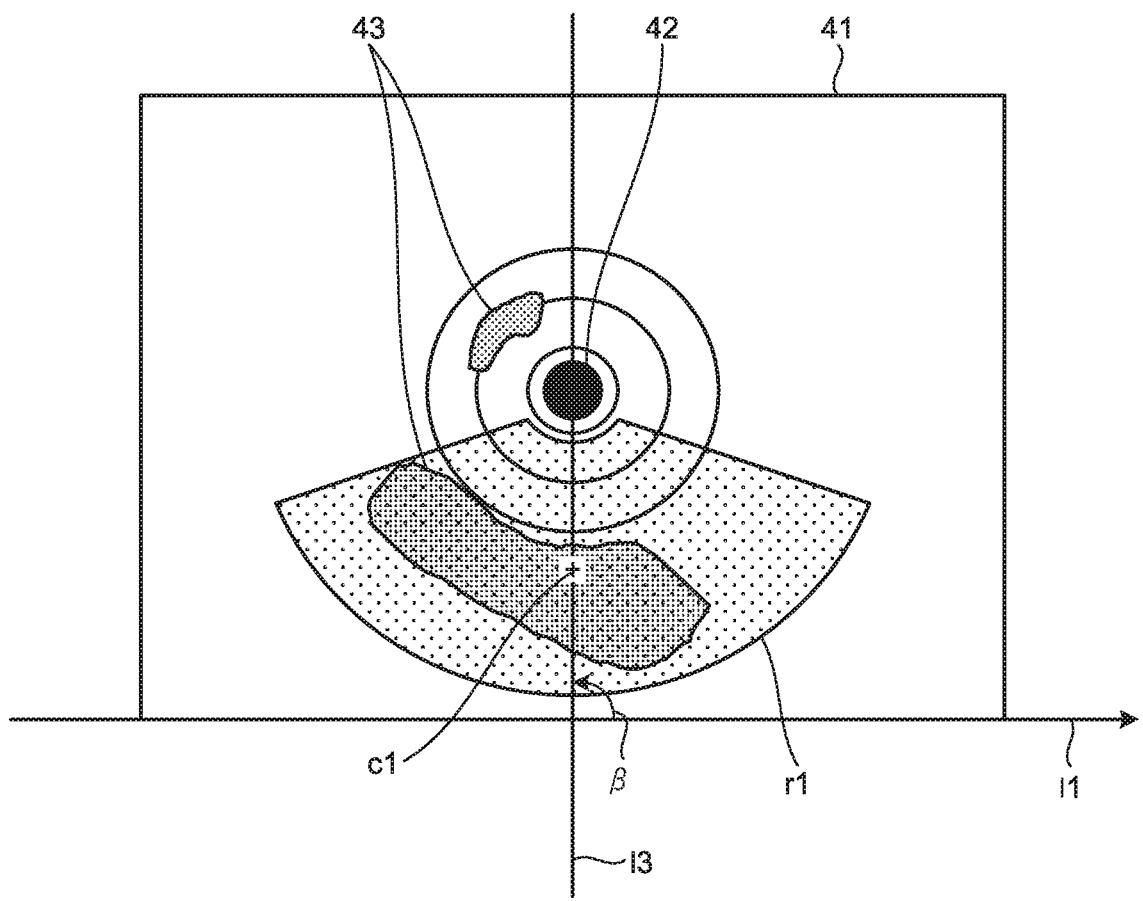
FIG. 6 is a diagram for explaining an ROI angle.

FIG. 6 is a diagram for explaining the ROI angle. As illustrated in FIG. 6, the angle formed by the straight line l1 (reference line) and a straight line l3 (second straight line) the straight line l1 is a ROI angle β, the straight line l1 extending in the horizontal direction corresponding to the horizontal side of the operation screen of the touch pad 51 in the ultrasound image 41, the straight line l3 passing through the center c1 of the ROI r1 and the central position of the ultrasound transducer area 42. Herein, as in the case of the contact angle α, for the angle formed by the straight line l1 and the straight line l3, the contact angle β with respect to the straight line l1 is defined within a range of 0°≤β<180°, with the counterclockwise direction being set as a positive direction.

When the relative relationship between the contact angle α and the ROI angle β meets a given condition, the operation controller 34 reduces or increases the shape of the ROI r1 in a direction along the reference axis. When the relative relationship between the contact angle α and the ROI angle β does not meet the given condition, the operation controller 34 reduces or increases the shape of the ROI r1 in a direction orthogonal to the reference axis. The reference axis is a straight line passing through the center line c1 and the central position of the ultrasound transducer area 42 and is the straight line l3 in FIG. 6. The given condition is that, for example, an absolute value |α−β| of α−β that is the relative relationship between the contact angle α and the ROI angle β meets any one of 0°≤|α−β|≤45° and 135°≤|α−β|<180°.

The controller 35 controls the entire ultrasound diagnostic system 1. The controller 35 is achieved using a CPU having operational and control functions and various operational circuits. The controller 35 reads information that is stored in the storage 36 and executes various types of operational processing relating to the operation method of the ultrasound observation apparatus 3, thereby overall controlling the ultrasound observation apparatus 3. The controller 35 can be configured using a CPU shared with the display controller 32 and the operation controller 34, etc.

The storage 36 stores various programs for causing the ultrasound diagnostic system 1 to operate and data containing various parameters necessary for operations of the ultrasound diagnostic system 1, etc. The storage 36, for example, stores an initial position (sound ray number) of a write start position (position in which ultrasound transmission starts) of the ultrasound image 41.

The storage 36 stores various programs containing the operation program for executing an operation method of the ultrasound diagnostic system 1. The operation program may be also recordable in a computer-readable recording medium, such as a hard disk, a flash memory, a CD-ROM, a DVD-ROM or a flexible disk, and thus may be widely distributable. The above-described various programs can be acquired by being downloaded via a communication network. The communication network herein is achieved with, for example, an existing public network, a local area network (LAN), a wide area network (WAN), or the like, and it does not matter whether the communication network is wired or wireless.

The storage 36 having the above-described configuration is achieved using a read only memory (ROM) in which various programs, etc., are installed in advance, a random access memory (RAM) that stores operational processing parameters and data for each set of processing, etc.

The display 4 is connected to the ultrasound observation apparatus 3. The display 4 is configured using a display panel that is formed of liquid crystals, organic electro luminescence (EL), or the like. The display 4, for example, displays various types of information relating to operations, such as the ultrasound image 41 that is output by the ultrasound observation apparatus 3.

As illustrated in FIG. 2, the body of the input device 5 is a housing and whose outer surface is water-tightly covered with a cover made of silicon. The input device 5 includes the touch pad 51 that senses contact of a contacting object, such as fingers of the operator, and a display unit 52 that can display various types of information. The operation screen of the touch pad 51 is square or rectangular. The input device 5 is electrically connected to the ultrasound observation apparatus 3 via a cable and outputs, to the input unit 33, a signal of an instruction input to the touch pad 51.

When a contacting object, such as fingers of the operator, makes contact with the touch pad 51, the input device 5 senses a contact position using a contact sensor and outputs the contact position to the ultrasound observation apparatus 3. When the contacting object moves while making contact with the touch pad 51, the input device 5 senses a direction and an amount of the move and outputs the direction and amount to the ultrasound observation apparatus 3. Based on the received information, the ultrasound observation apparatus 3 performs signal processing corresponding to the input contact position and the direction and amount of move of the contact position. For example, based on the received information, the ultrasound observation apparatus 3 outputs an image obtained by sliding or rotating the position of the image to be displayed on the display 4.

The display unit 52 displays setting of an observation mode, setting of an observation condition, etc. The display unit 52 may be formed of a touch panel and may be configured to change the observation mode setting, the observation condition setting, etc.

Figure 7:
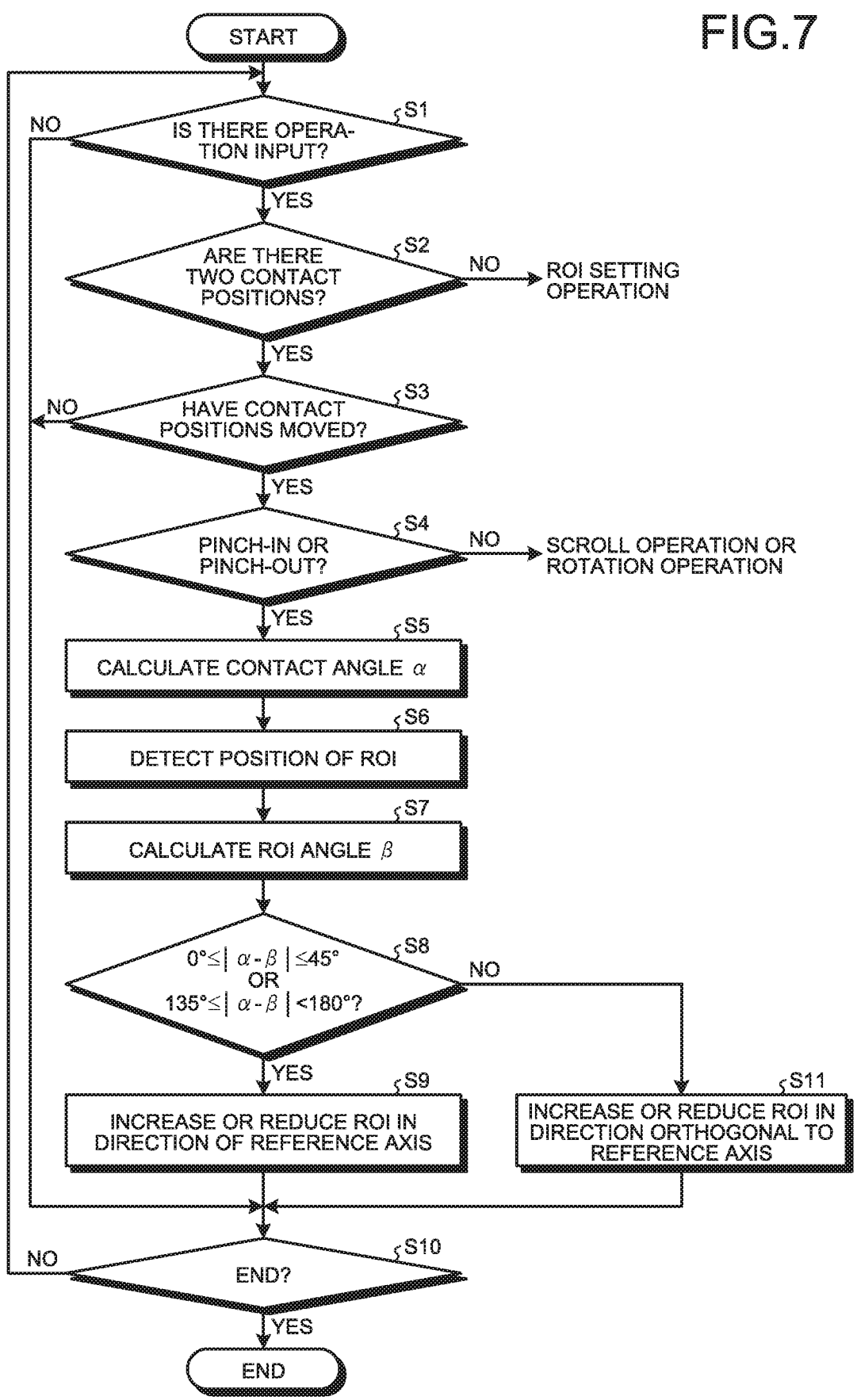
FIG. 7 is a flowchart of operations of the ultrasound observation apparatus according to the first embodiment of the disclosure.

An operation of reducing and increasing the ROI r1 in the ultrasound image 41 that is displayed on the display 4 will be described in detail. FIG. 7 is a flowchart of operations of the ultrasound observation apparatus according to the first embodiment of the present disclosure. As illustrated in FIG. 7, first of all, the controller 35 determines whether there is an operation input (step S1). Specifically, the controller 35 determines whether an operation input to the touch pad 51 of the input device 5 is input via the input unit 33.

When it is determined that there is an operation input (YES at step S1), the controller 35 determines whether there are two contact positions (step S2). Specifically, the controller 35 acquires, via the input unit 33, an operation input to the touch pad 51 of the input device, causes the contact position detector 341 to detect contact positions, and determines whether the contact positions detected by the contact position detector 341 are two.

When the controller 35 determines that there are two contact positons (YES at step S2), the controller 35 then determines whether the contact positions have moved (step S3). Specifically, the controller 35 determines whether contact positions detected by the contact position detector 341 have moved.

When the controller 35 determines that the contact positions have moved (YES at step S3), the controller 35 determines whether an operation on the touch pad 51 is a pinch-in operation or a pinch-out operation (step S4). Specifically, the controller 35 determines whether the two contact positions that are detected by the contact position detector 341 have moved to get close to each other or have moved to separate from each other.

When the controller 35 determines that the operation on the touch pad 51 is a pinch-in operation or a pinch-out operation (YES at step S4), the controller 35 causes the contact angle calculator 342 to calculate a contact angle $\alpha$ (step S5). Furthermore, the controller 35 causes the ROI detector 343 to detect a positon of an ROI (step S6) and causes the ROI angle calculator 344 to calculate a ROI angle $\beta$ (step S7).

The controller 35 then determines whether the relative relationship ($|\alpha-\beta|$) between the contact angle $\beta$ and the ROI angle $\beta$ is within the range where $0°\leq|\alpha-\beta|\leq45°$ or $135°\leq|\alpha-\beta|<180°$ is met (step S8).

When the controller 35 determines that the relative relationship ($|\alpha-\beta|$) meets $0°\leq|\alpha-\beta|\leq45°$ or $135°\leq|\alpha-\beta|<180°$ (YES at step S8), the controller 35 causes the operation controller 34 to reduce or increase the shape of the ROI along a reference axis (step S9).

First of all, the case where, when an ROI is in a lower part of the ultrasound image 41 (in a 6-o'clock direction), a pinch-in operation that meets $0°\leq|\alpha-\beta|\leq45°$ or $135°\leq|\alpha-\beta|<180°$ is performed will be described. Assume that, when the ROI r1 illustrated in FIG. 3 is in a lower part of the ultrasound image 41 (in the 6-o'clock direction), a vertical pinch-in operation is performed on the operation screen of the touch pad 51 illustrated in FIG. 4. As illustrated in FIGS. 5 and 6, the contact angle $\alpha$ and the ROI angle $\beta$ are approximately 90° and $|\alpha-\beta|$ is approximately 0°. Thus, $0°\leq|\alpha-\beta|\leq45°$ or $135°\leq|\alpha-\beta|<180°$ is met and the shape of the ROI r1 is reduced along the reference axis.

Figure 8:
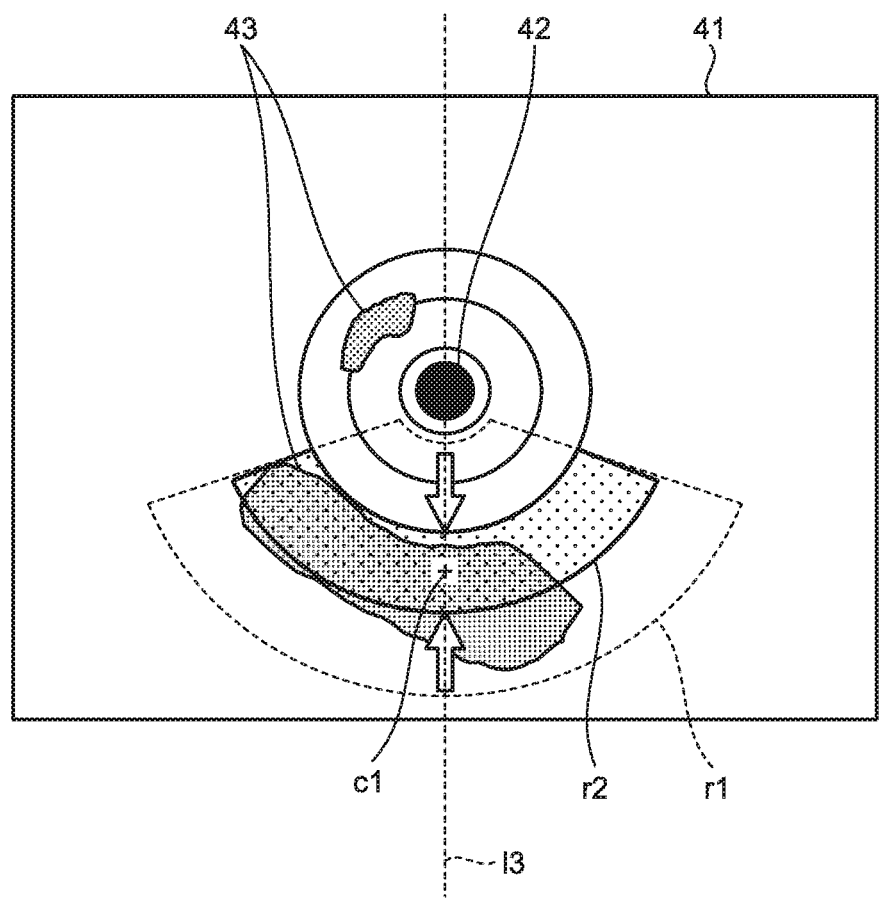
FIG. 8 is a diagram illustrating that, when an ROI is in a lower part of an ultrasound image, the shape of the ROI is reduced in a direction along a reference axis.

FIG. 8 is a diagram illustrating that, when an ROI is in a lower part of an ultrasound image, the shape of the ROI is reduced along a reference line. As illustrated in FIG. 8, the controller 35 causes the operation controller 34 to reduce the shape of the ROI r1 along the reference axis (the straight line l3 in FIG. 8) to an ROI r2.

Figure 9:
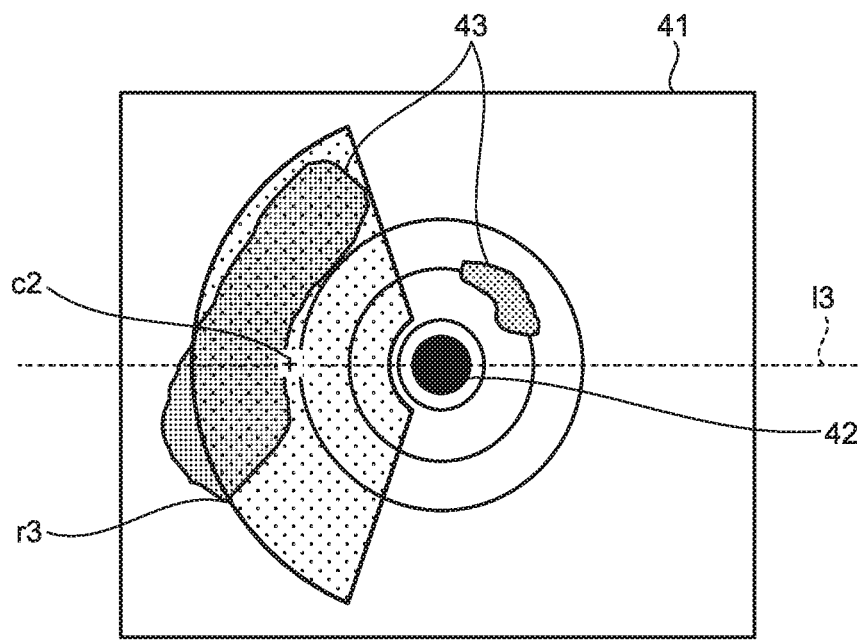
FIG. 9 is a diagram illustrating that an ROI is set on the left in an ultrasound image.
Figure 10:
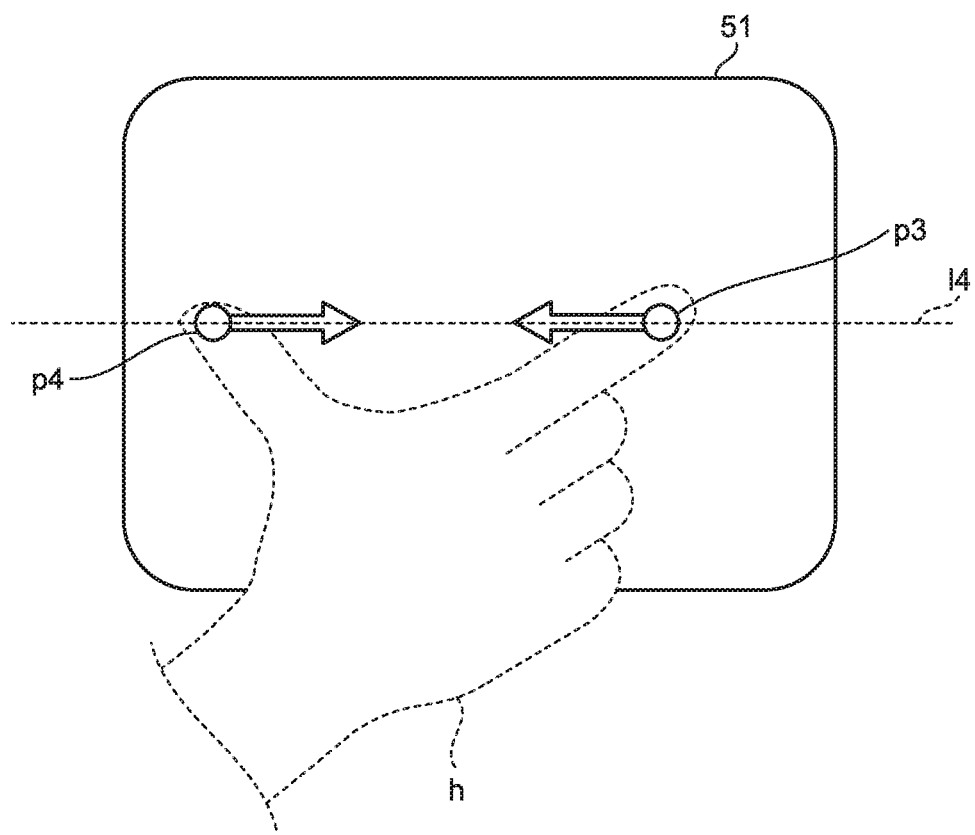
FIG. 10 is a diagram illustrating that an operator performs a pinch-in operation in the horizontal direction on an operation screen of the touch pad.

Subsequently, the case where, when an ROI is on the left side (in a 9-o'clock direction) in the ultrasound image 41, a pinch-in operation that meets $0°\leq|\alpha-\beta|\leq45°$ or $135°\leq|\alpha-\beta|<180°$ is performed will be described. FIG. 9 is a diagram illustrating that an ROI is set on the left in an ultrasound image. In FIG. 9, the straight line l3 passing through a center c2 of an ROI r3 and the central position of the ultrasound transducer area 42 is a straight line extending in the horizontal direction in FIG. 9 and accordingly the ROI angle $\beta$ is approximately 0°. FIG. 10 is a diagram illustrating that the operator performs a pinch-in operation in the horizontal direction of the operation screen of the touch pad. In FIG. 10, a straight line l4 passing though the centers of two contact positions (a point p3 and a point p4) in the touch pad 51 is a straight line extending in the horizontal direction in FIG. 10 and thus the contact angle α is approximately 0°.

Assume that, when the ROI r3 illustrated in FIG. 9 is on the left (in the 9-o'clock direction) in the ultrasound image 41, a pinch-in operation in the horizontal direction on the operation screen of the touch pad 51 illustrated in FIG. 10 is performed. The contact angle α and the ROI angle β are approximately 0° and |α−β| is approximately 0°. Thus, 0°≤|α−β|≤45° or 135°≤|α−β|<180° is met and the shape of the ROI r3 is reduced in a direction along the reference axis.

Figure 11:
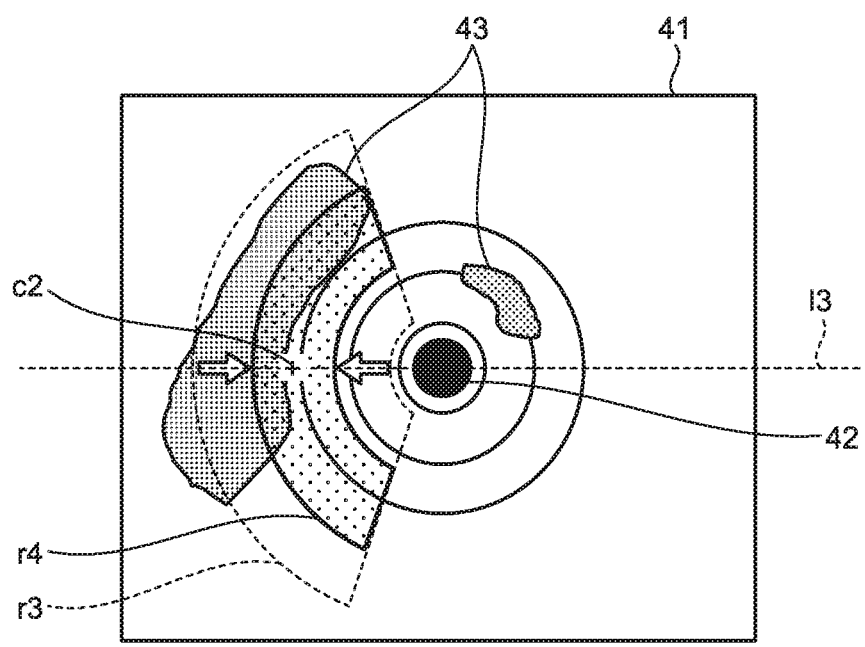
FIG. 11 is a diagram illustrating that, when an ROI is on the left of an ultrasound image, the shape of the ROI is reduced in a direction along a reference axis.

FIG. 11 is a diagram illustrating that, when an ROI is on the left in an ultrasound image, the shape of the ROI is reduced in a direction along a reference axis. As illustrated in FIG. 11, the controller 35 causes the operation controller 34 to reduce the shape of the ROI r3 in a direction along the reference axis (the straight line l3 in FIG. 11) to a ROI r4.

The controller 35 then determines whether there is an end instruction input (step S10) and, when the controller 35 determines that there is an end instruction input (YES at step S10), a process series ends. On the other hand, when the controller 35 determines that there is not any end instruction input (NO at step S10), the controller 35 returns to step S1 and the process continues.

At step S8, when the controller 35 determines that the relative relationship (|α−β|) meets neither 0°≤|α−β|≤45° nor 135°≤|α−β|<180° (NO at step S8), the controller 35 causes the operation controller 34 to reduce or increase the shape of the ROI in a direction orthogonal to the reference axis (step S11).

First of all, the case where, when an ROI is in a lower part of the ultrasound image 41 (in the 6-o'clock direction), a pinch-in operation that meets neither 0°≤|α−β|≤45° nor 135°|α−β|<180° is performed will be described. Assume that, when the ROI r1 illustrated in FIG. 8 is in a lower part of the ultrasound image 41 (in the 6-o'clock direction), a horizontal pinch-in operation is performed on the operation screen of the touch pad 51 illustrated in FIG. 10. The contact angle α is approximately 0°, the ROI angle β is approximately 90°, and |α−β| is approximately 90°. Thus, neither 0°≤|α−β|≤45° nor 135°≤|α−β|<180° is met and the shape of the ROI r2 is reduced along the direction orthogonal to the reference axis.

Figure 12:
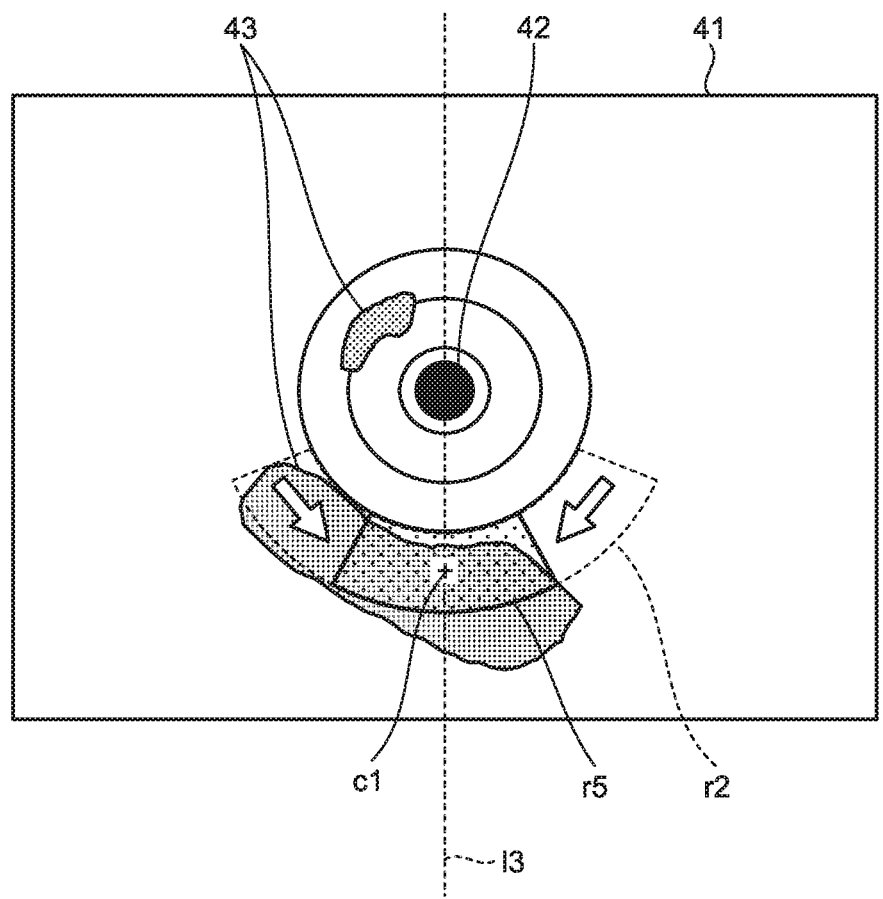
FIG. 12 a diagram illustrating that, when an ROI is in a lower part of an ultrasound image, the shape of the ROI is reduced in a direction orthogonal to the reference axis.

FIG. 12 is a diagram illustrating that, when an ROI is in a lower part of an ultrasound image, the shape of the ROI is reduced in a direction orthogonal to a reference axis. As illustrated in FIG. 12, the controller 35 causes the operation controller 34 to reduce the shape of the ROI r2 in the direction orthogonal to the reference axis (the straight line l3 in FIG. 12) to an ROI r5.

Subsequently, the case where, when an ROI is on the left side (in the 9-o'clock direction) in the ultrasound image 41, a pinch-in operation that meets neither 0°≤|α−β|≤45° nor 135°≤|α−β|<180° is performed will be described. When the ROI r4 illustrated in FIG. 11 is on the left side (in the 9-o'clock direction) in the ultrasound image 41, a vertical pinch-in operation on the operation screen of the touch pad 51 illustrated in FIG. 4 is performed. The contact angle α is approximately 90°, the ROI angle β is approximately 0°, and |α−β| is approximately 90°. Accordingly, neither 0°≤|α−β|≤45° nor 135°≤|α−β|<180° is met and the shape of the ROI r4 is reduced in the direction orthogonal to the reference axis.

Figure 13:
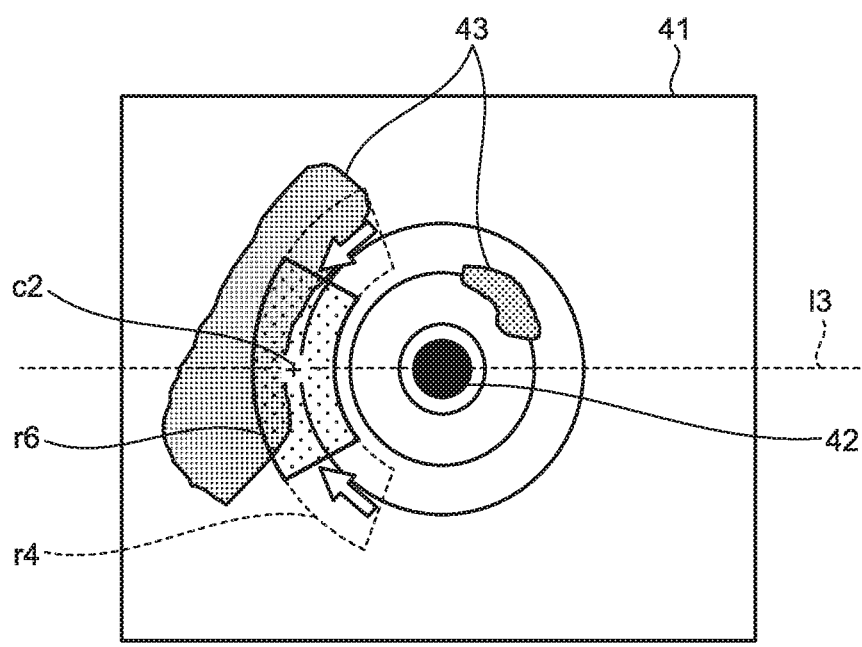
FIG. 13 a diagram illustrating that, when an ROI is in a lower part of an ultrasound image, the shape of the ROI is reduced in a direction orthogonal to the reference axis.

FIG. 13 is a diagram illustrating that, when an ROI is on the left in an ultrasound image, the shape of the ROI is reduced in a direction orthogonal to a reference axis. As illustrated in FIG. 13, the controller 35 causes the operation controller 34 to reduce the shape of the ROI r4 in the direction orthogonal to the reference axis (the straight line l3 in FIG. 13) to an ROI r6.

Thereafter, end determination at step S10 is performed and the process ends or is continued.

At step S2, when the controller 35 determines that there are not two contact positions (NO at step S2), that is, when there is one contact position, for example, the controller 35 causes the operation controller 34 to perform an ROI setting operation to change the position at which the ROI is set according to an operation input. Note that, when there are three or more contact positions, it may be determined that there is no operation input.

In the case where, at step S4, the controller 35 determines that the operation on the touch pad 51 is neither a pinch-in operation nor a pinch-out operation (NO at step S4), when the operation on the touch pad 51 is a scroll operation (when the two contact positions move in the same direction), the controller 35 causes the operation controller 34 to perform a scroll operation to perform scroll move on the central position of the ultrasound image 41 and, when the operation on the touch pad 51 is a rotation operation (when the two contact positions move in a circumferential direction), the controller 35 causes the operation controller 34 to perform a rotation operation to rotate the ultrasound image 41 about the central position of the ultrasound transducer area 42.

At the step of determining whether there is an operation input (step S1), when no operation has been performed for a given time or more (NO at step 1) and, at the step of determining whether the contact positions have moved (step S3), when the contact positons have not moved for a given time or more (NO at step S3), the end determination at step S10 is made and the process series ends or is continued.

As described above, according to the first embodiment, the direction of a pinch-in operation or a pinch-out operation performed by the operator and the direction in which the ROI in the ultrasound image 41 is reduced or increased approximately agree with each other and thus it is possible to perform an instinctive operation when reducing or increasing the ROI.

Modification 1-1

Figure 14:
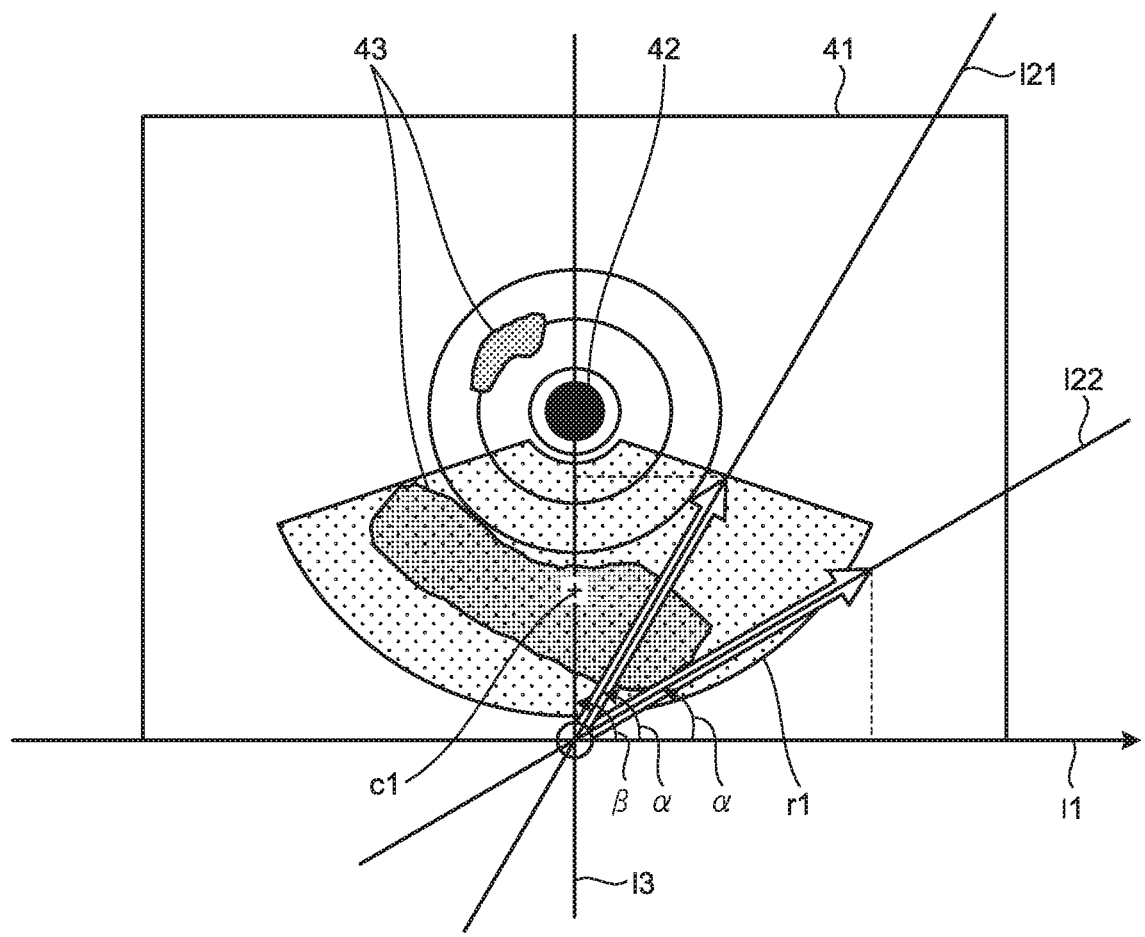
FIG. 14 is a diagram for explaining operations of an ultrasound observation apparatus according to Modification 1-1 of the first embodiment of the disclosure.

In the first embodiment, according to the relative relationship (|α−β|), the amount by which the ROI is reduced or increased may be changed with respect to the pinch-in operation or the pinch-out operation. FIG. 14 is a diagram for explaining operations of an ultrasound observation apparatus according to Modification 1-1 of the first embodiment of the disclosure. As illustrated in FIG. 14, the direction of a pinch-in operation is a direction along a straight line l21 and, when a pinch-in operation that meets 0°≤|α−β|≤45° or 135°≤|α−β|<180° is performed, an amount of move of the fingers for the pinch-in operation may be multiplied by cos(|α−β|) serving as a coefficient to reduce an ROI.

Similarly, when the direction of the pinch-in operation is a direction along a straight line l22 and a pinch-in operation that meets neither 0°≤|α−β|≤45° nor 135°≤|α−β|<180°, an amount of move of the fingers for the pinch-in operation may be multiplied by sin(|α−β|) serving as a coefficient to reduce an ROI.

According to Modification 1-1 described above, the amount of deformation of the ROI varies according to the direction of the pinch-in operation and this enables the operator to perform a more instinctive operation.

Second Embodiment

A second ultrasound diagnostic system according to a second embodiment will be described. The ultrasound diagnostic system may have the same configuration as that of the ultrasound diagnostic system 1 according to the first embodiment illustrated in FIG. 1 and thus description thereof will be omitted as appropriate.

Note that, in the ultrasound diagnostic system 1, the operation controller 34 reduces or increases the shape of an ROI in a direction along a reference axis and in a direction orthogonal to the reference axis, based on the relative relationship ($|\alpha-\beta|$).

Figure 15:
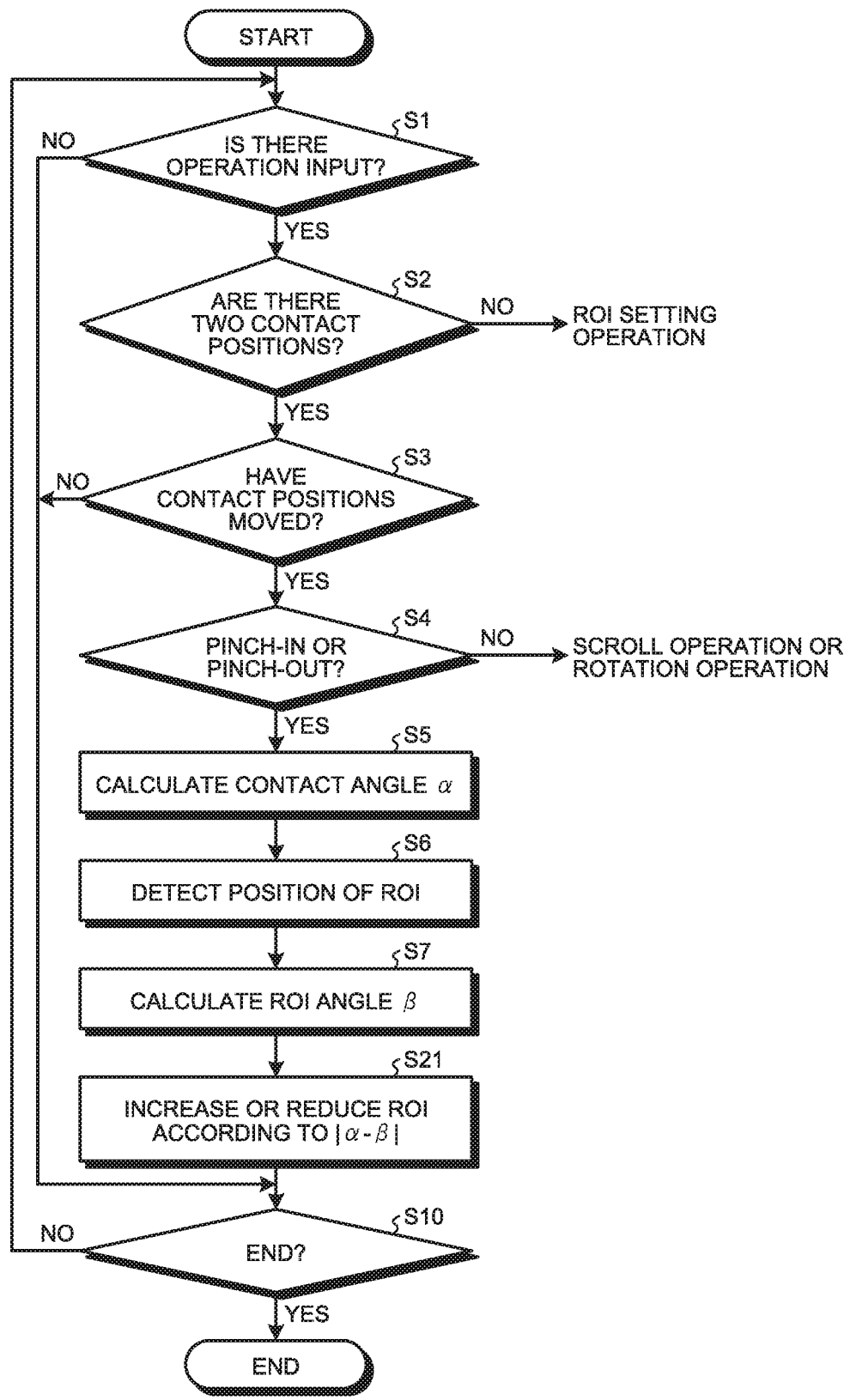
FIG. 15 is a flowchart of operations of an ultrasound observation apparatus according to a second embodiment of the disclosure.

FIG. 15 is a flowchart of operations of the ultrasound observation apparatus according to a second embodiment of the present disclosure. As illustrated in FIG. 15, after the same process as that of the first embodiment is performed until step S7, the controller 35 causes the operation controller 34 to reduce or increase the shape of the ROI in both the direction along the reference axis and the direction orthogonal to the reference axis (step S21).

Figure 16:
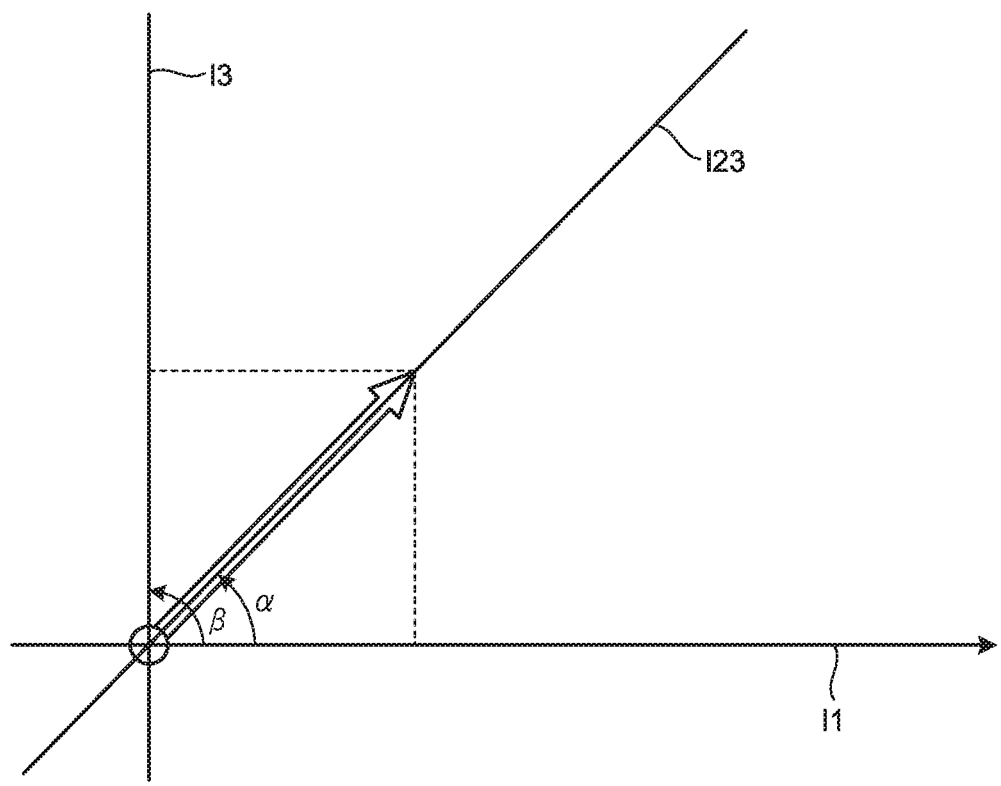
FIG. 16 is a diagram for explaining operations of the ultrasound observation apparatus according to the second embodiment of the disclosure.

FIG. 16 is a diagram for explaining operations of the ultrasound observation apparatus according to the second embodiment of the present disclosure. As illustrated in FIG. 16, when the direction of a pinch-in operation is a direction along a straight line l23, the amount of move of the fingers for the pinch-in operation may be multiplied by $\cos(|\alpha-\beta|)$ serving as a coefficient to reduce the ROI along the direction of the reference axis (the straight line l3 in FIG. 16) and may be multiplied by $\sin(|\alpha-\beta|)$ serving as a coefficient to reduce the ROI in the direction (the straight line l1 in FIG. 16) orthogonal to the reference axis.

Figure 17:
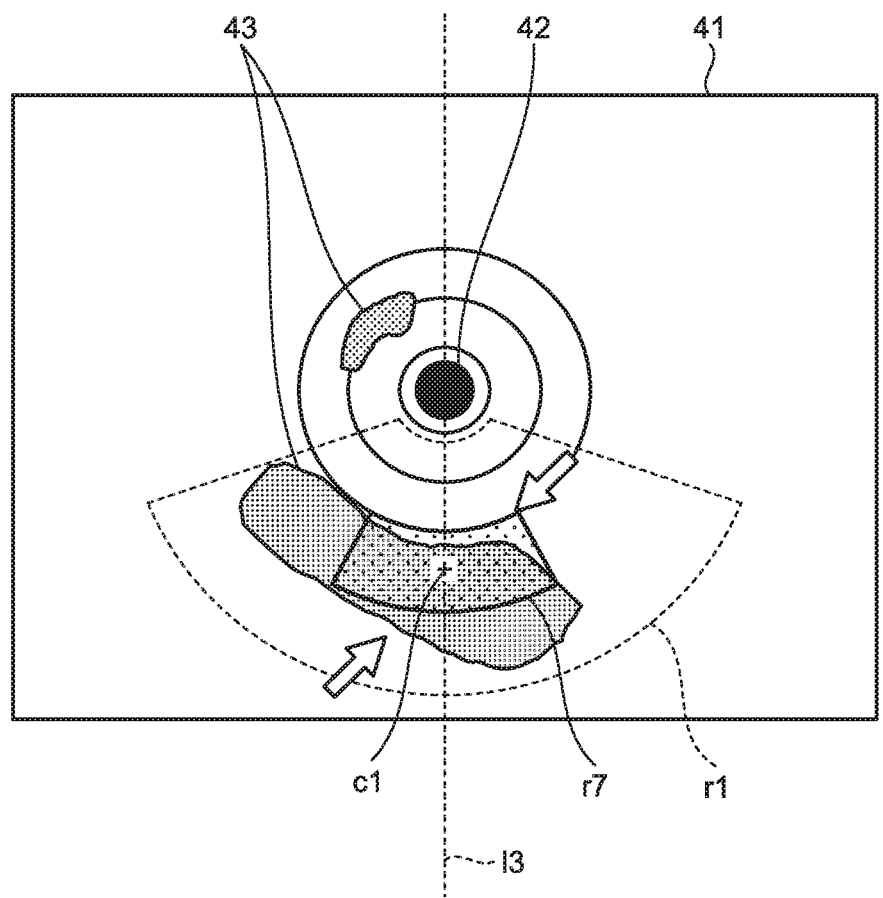
FIG. 17 is a diagram illustrating that, when an ROI is in a lower part of an ultrasound image, the shape of the ROI is reduced in a direction along the reference axis and in a direction orthogonal to the reference axis.

FIG. 17 is a diagram illustrating that, when an ROI is in a lower part of an ultrasound image, the shape of the ROI is reduced in a direction along a reference axis and a direction orthogonal to the reference axis. Assume that, as illustrated in FIG. 17, when the ROI r1 is in a lower part (in the 6-o'clock direction) of the ultrasound image 41, the pinch-in operation illustrated in FIG. 16 is performed. The controller 35 causes the operation controller 34 to, based on the relative relationship ($|\alpha-\beta|$), make a reduction by a product of the amount of move of the fingers for the pinch-in operation by $\cos(|\alpha-\beta|)$ serving as a coefficient to reduce the ROI in the direction of the reference axis (the straight line l3 in FIG. 17) and make a reduction by a product of the amount of move of the fingers for the pinch-in operation by $\sin(|\alpha-\beta|)$ serving as a coefficient to reduce the ROI in the direction orthogonal to the reference axis, thereby achieving a ROI r7. In other words, the controller 35 causes the operation controller 34 to reduce or increase the shape of the ROI along the direction in which the pinch-in operation is performed based on the relative relationship ($|\alpha-\beta|$).

As described above, according to the second embodiment, the shape of the ROI deforms according to the direction of the pinch-in operation and this enables the operator to perform a more instinctive operation.

Third Embodiment

An ultrasound diagnostic system according to a third embodiment will be described. The ultrasound diagnostic system may have the same configuration as that of the ultrasound diagnostic system 1 according to the first embodiment illustrated in FIG. 1, and thus description thereof will be omitted as appropriate.

Note that, in the ultrasound diagnostic system 1, under the control of the controller 35, the operation controller 34 reduces or increases the shape of an ROI in a direction along a reference axis when the relative relationship ($|\alpha-\beta|$) meets a first condition that is any one of $0°\leq|\alpha-\beta|\leq15°$ and $165°\leq|\alpha-\beta|<180°$ and the operation controller 34 reduces or increases the shape of the ROI in a direction orthogonal to the reference axis when the relative relationship ($|\alpha-\beta|$) meets a second condition that is $75°\leq|\alpha-\beta|\leq105°$. Under the control of the controller 35, the operation controller 34 reduces or increases the shape of the ROI in the direction along the reference axis and in the direction orthogonal to the reference axis when the relative relationship ($|\alpha-\beta|$) meets neither $0°\leq|\alpha-\beta|\leq15°$ nor $75°\leq|\alpha-\beta|\leq105°$ nor $165°\leq|\alpha-\beta|<180°$.

Figure 18:
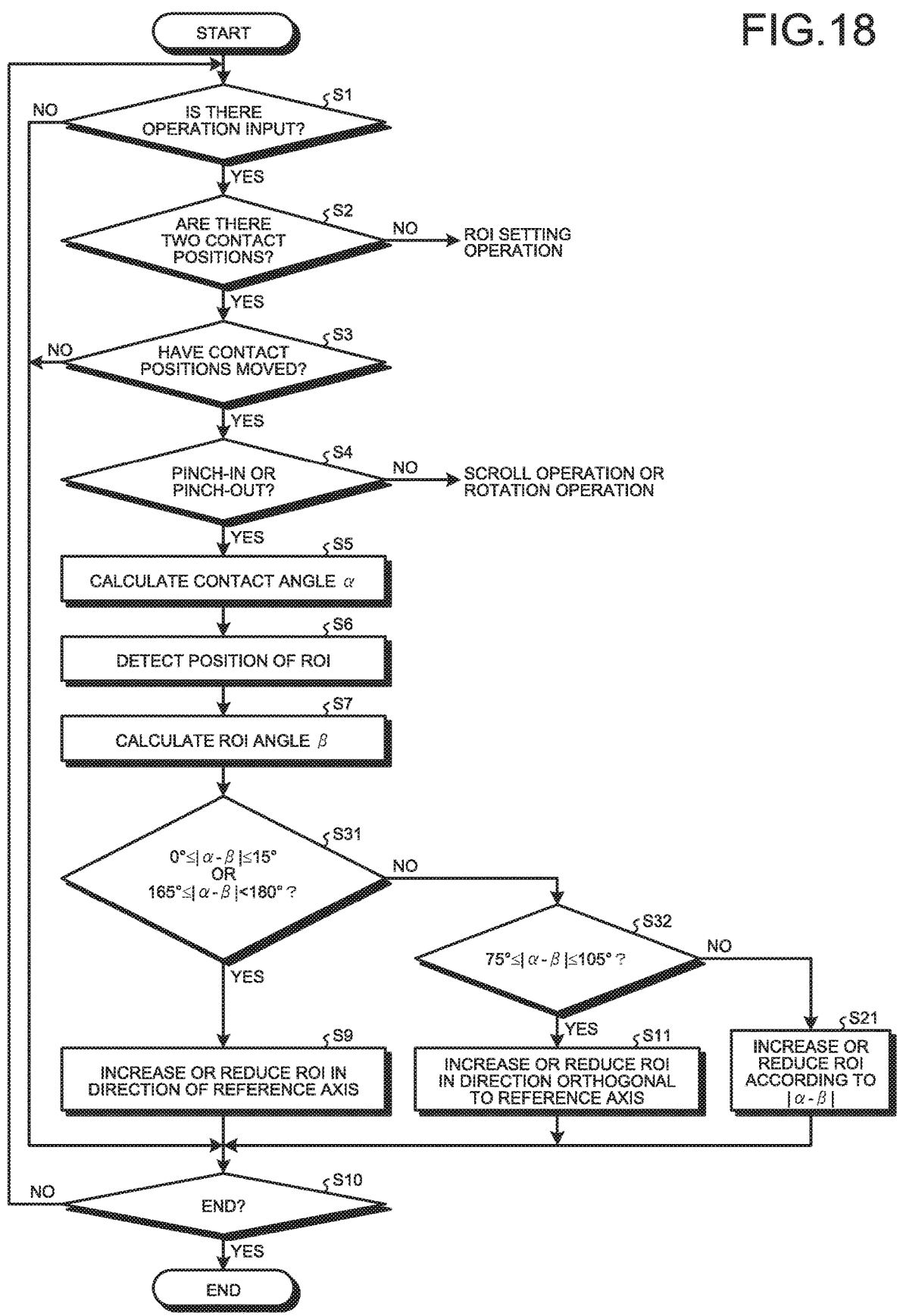
FIG. 18 is a flowchart of operations of an ultrasound observation apparatus according to a third embodiment of the disclosure.

FIG. 18 is a flowchart of operations of an ultrasound observation apparatus according to a third embodiment of the disclosure. As illustrated in FIG. 18, after the same process as that of the first embodiment is performed until step S7, the controller 35 determines whether the relative relationship $|\alpha-\beta|$ between the contact angle α and the ROI angle β is within a range where $0°\leq|\alpha-\beta|\leq15°$ or $165°\leq|\alpha-\beta|<180°$ is met (step S31).

When the controller 35 determines that the relative relationship ($|\alpha-\beta|$) meets $0°\leq|\alpha-\beta|\leq15°$ or $165°\leq|\alpha-\beta|<180°$ (YES at step S31), the controller 35 causes the operation controller 34 to reduce or increase the shape of the ROI in a direction along a reference axis (step S9).

When the controller 35 determines that the relative relationship ($|\alpha-\beta|$) meets neither $0°\leq|\alpha-\beta|\leq15°$ nor $165°\leq|\alpha-\beta|<180°$ (NO at step S31), the controller 35 determines whether the relative relationship ($|\alpha-\beta|$) between the contact angle α and the ROI angle β is within the range where $75°\leq|\alpha-\beta|\leq105°$ is met (step S32).

When the controller 35 determines that the relative relationship ($|\alpha-\beta|$) meets $75°\leq|\alpha-\beta|\leq105°$ (YES at step S32), the controller 35 causes the operation controller 34 to reduce or increase the shape of the ROI in the direction orthogonal to the reference axis (step S11).

Furthermore, when the controller 35 determines that the relative relationship ($|\alpha-\beta|$) does not meet $75°|\alpha-\beta|\leq105°$ (NO at step S32), the controller 35 causes the operation controller 34 to reduce or increase the shape of the ROI in the direction along the reference axis and in the direction orthogonal to the reference axis (step S21).

As described above, according to the third embodiment, the ROI is reduced or increased easily in the direction along the reference axis and in the direction orthogonal to the reference axis and the shape of the ROI can be modified according to the direction of a pinch-in operation, which achieves high operability.

According to the disclosure, it is possible to achieve an ultrasound observation apparatus, an operation method of an ultrasound observation apparatus, and an operation program for an ultrasound observation apparatus that enable an instinctive operation when reducing or increasing a region of interest.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus configured to cause a display to display an ultrasound image that is generated based on an ultrasound signal that is received from an ultrasound transducer configured to transmit ultrasound to a subject to be observed and receive the ultrasound that is reflected from the subject to be observed, the ultrasound observation apparatus comprising:

an operation controller configured to control a shape of a region of interest that is set in the ultrasound image according to a change in a contact position at which a contacting object contacts a touch pad, the operation controller being configured to detect two contact positions of the contacting object on the touch pad, calculate a first positional relationship based on the two contact positions in the touch pad, wherein a contact angle is the first positional relationship formed by a first straight line and a reference line, the first straight line passing through both centers of the two contact positions in the touch pad, detect a position of the region of interest that is set in the ultrasound image, calculate a second positional relationship based on a position at which the region of interest is set and on a reference position, wherein a region of interest angle is the second positional relationship formed by a second straight line and the reference position, the second straight line passing through both the reference position and a center of the region of interest, and control the shape of the region of interest based on a relative relationship between the first positional relationship and the second positional relationship;

wherein:

when the relative relationship meets a given condition, the operation controller is configured to reduce or increase the shape of the region of interest in a direction along a reference axis, and when the relative relationship does not meet the given condition, the operation controller is configured to reduce or increase the shape of the region of interest in a direction orthogonal to the reference axis.

2. The ultrasound observation apparatus according to claim 1, wherein the given condition comprises a first condition and a second condition, the, wherein when the relative relationship meets the first condition, the operation controller is configured to reduce or increase the shape of the region of interest in a direction along a reference axis, when the relative relationship meets the second condition, the operation controller is configured to reduce or increase the shape of the region of interest in a direction orthogonal to the reference axis, and when the relative relationship meets neither the first condition nor the second condition, the operation controller is configured to reduce or increase the shape of the region of interest in a direction along the reference axis and in a direction orthogonal to the reference axis based on the relative relationship.

3. The ultrasound observation apparatus according to claim 1, wherein an operation screen of the touch pad is square or rectangular, and the reference line is a straight line corresponding to a vertical side or a horizontal side of the operation screen of the touch pad.

4. The ultrasound observation apparatus according to claim 1, wherein the reference position is a central position of an ultrasound transducer area that corresponds to the ultrasound transducer and that is in the ultrasound image displayed on the display.

5. The ultrasound observation apparatus according to claim 1, wherein the region of interest has a shape obtained by excluding a first circular sector from a second circular sector, the first and second circular sectors being circular sectors whose centers are a same as a central position of an ultrasound transducer area that corresponds to the ultrasound transducer and that is in the ultrasound image displayed on the display, the first and second circular sectors having a same central angle but having different radii, the first circular sector having a smaller radius than the second circular sector.

6. The ultrasound observation apparatus according to claim 5, wherein the center of the region of interest is a point at a center of the region of interest in a radial direction of the ultrasound transducer area and in an azimuth direction of the ultrasound transducer area.

7. The ultrasound observation apparatus according to claim 1, wherein the operation controller is configured to control a ratio of a size of the region of interest to the ultrasound image.

8. The ultrasound observation apparatus according to claim 1, wherein the operation controller is configured to set, as the region of interest, an area where analysis processing is to be performed on the ultrasound image.

9. The ultrasound observation apparatus according to claim 8, wherein the operation controller is configured to set, as the region of interest, the area where the analysis processing based on acoustic characteristics is to be performed on the ultrasound image.

10. The ultrasound observation apparatus according to claim 9, wherein the operation controller is configured to generate an elasticity image corresponding to hardness of the subject, and superimpose the generated elasticity image on the region of interest.

11. An operation method of an ultrasound observation apparatus configured to cause a display to display an ultrasound image that is generated based on an ultrasound signal that is received from an ultrasound transducer configured to transmit ultrasound to a subject to be observed and receive the ultrasound that is reflected from the subject to be observed, the method comprising:

by an operation controller, detecting two contact positions at which a contacting object contacts a touch pad;

by the operation controller, calculating a first positional relationship based on the two contact positions in the touch pad, wherein a contact angle is the first positional relationship formed by a first straight line and a reference line, the first straight line passing through both centers of the two contact positions in the touch pad;

by the operation controller, detecting a position of the region of interest that is set in the ultrasound image, by the operation controller, calculating a second positional relationship based on a position at which the region of interest is set and on a reference position, wherein a region of interest angle is the second positional relationship formed by a second straight line and the reference position, the second straight line passing through both the reference position and a center of the region of interest; and by the operation controller, controlling a shape of the region of interest that is set in the ultrasound image based on a relative relationship between the first positional relationship and the second positional relationship;

wherein:

when the relative relationship meets a given condition, the operation controller controls the shape of the region of interest to reduce or increase the shape of the region of interest in a direction along a reference axis, and when the relative relationship does not meet the given condition, the operation controller controls the shape of the region of interest to reduce or increase the shape of the region of interest in a direction orthogonal to the reference axis.

* * * * *